(12) United States Patent
Chen et al.

(10) Patent No.: US 6,864,088 B2
(45) Date of Patent: Mar. 8, 2005

(54) FAST METHOD OF TRANSFORMING COMPETENT CELLS

(75) Inventors: Tzu-Chih Chen, Taipei (TW); Wei-Ni Hua, Taipei (TW)

(73) Assignee: Yeastern Biotech Co., Ltd., Taipei (TW)

( * ) Notice: Subject to any disclaimer, the term of this patent is extended or adjusted under 35 U.S.C. 154(b) by 95 days.

(21) Appl. No.: 10/157,421

(22) Filed: May 29, 2002

(65) Prior Publication Data

US 2003/0138956 A1 Jul. 24, 2003

(30) Foreign Application Priority Data

Nov. 9, 2001 (TW) ........................................ 90127915 A

(51) Int. Cl.$^7$ ........................... C12N 15/64; C12N 15/70
(52) U.S. Cl. ......................... 435/488; 435/471; 435/476
(58) Field of Search ................................ 435/488, 471, 435/476, 320.1, 479, 485, 486, 487

(56) References Cited

FOREIGN PATENT DOCUMENTS

WO          0073414          5/2000

OTHER PUBLICATIONS

Zenilman et al., J. Gen. Appl. Microbiol., 29:233–243 (1983).*
Kitayama et al., J. Bacteriol., 155 (3):1200–1207 (19930.*
Huff et al., Biotechniques 9 (5):570–578 (1990).*
Pope, B. and Kent, H.M. High Efficiency 5 min Transformation of *Escherichia coli* High Efficiency 5 min Transformation of *Escherichia coli* Nucleic Acids Research, 1996, vol. 24, No. 3, pp. 536–537.
"Molecular Cloning, A Laboratory Manual", Sambrook et al, Cold Spring Harbor Laboratory Press, 1989, see Book 1 pp. 1.74–1.84, esp. pp. 1.79–1.81.
"Polyethylene Glycol–Mediated Bacterial Colony Transformation", Kurien & Scofield, Biotechnidques, 1995, vol. 18(6), pp. 1023–1024, 1026.
One Minute Transformation of Competent *E–coli* by Plasmid DNA, Golub, Nucleic Acids Research, 1988, vol. 16(4), p. 1641.
"High Efficiency Transformation of *Escherichia Coli* with Plasmids" by Hiroaki Inoue, Hiroshi Nojima and Hiroto Okayama, *Research Department , Turuga Enzyme Plant, Toyobo Co. Ltd. and Department of Molecular Genetics, Research Institute for Microbial diseases, Osaka University*, 1990, pp. 23–28.
"Competent and Supercompetent Cells", *Instruction Manual* of Stratagene, U.S.A.
"Plasmid Transformation of *Escherichia Coli* and Other Bacteria" by Douglas Hanahan, Joel Jessee and Fredric R. Bloom, *Methods In Enzymology*, vol. 204, pp. 63–114.
"E.Coloi Competent Cells" Technical Bulletin No. 095, *Promega Corporation*.
"One Minute Transformation of Competent *E.Coli* by Plasmid DNA" by Efirm I. Golub, *Yale University School of Medicine*, New Haven, CT, Dec. 1987.
"One–Step Preparation of Competent *Escherichia Coli*: Transformation and Storage of Bacterial Cells in the Same Solution" by C. t. Chung, Suzanne L. Niemela and roger H. Miller, *Proc. Natl. Acad. Sci. USA*, vol. 86, pp. 2172–2175, Apr. 1989.

* cited by examiner

*Primary Examiner*—James Ketter
*Assistant Examiner*—Nancy T. Vogel
(74) *Attorney, Agent, or Firm*—Thomas, Kayden, Horstemeyer & Risley

(57) ABSTRACT

A fast method of transforming competent cells is described. The competent cells are thawed at room temperature or in a water bath. Plasmid DNAs and competent cells are mixed together, then the mixture is subject to heat shock treatment. After plating the mixture on a low-temperature selective medium by a low-temperature plating tool, the competent cells are cultured on the selective medium.

16 Claims, No Drawings

FAST METHOD OF TRANSFORMING COMPETENT CELLS

CROSS-REFERENCE TO RELATED APPLICATION

This application claims the priority benefit of Taiwan application serial no. 90,127,915, filed Nov. 9, 2001, the full disclosure of which is incorporated herein by reference.

BACKGROUND

1. Field of Invention

The present invention relates to a gene transformation method. More particularly, the present invention relates to a fast method of transforming competent cells.

2. Description of Related Art

The host cells after preliminary treatment to be more permeable to DNA molecules are called competent cells, and the technology of delivering DNA molecules in the surrounding medium into host cells is called transformation. Hence, producing competent cells and transforming competent cells is very important in view of recent developments of genetic engineering.

The technology described above can be retraced to Mandel, M. and Higa, A. (*J. Mol. Biol.* 53:159–162), who published a chemical transformation method using $CaCl_2$. After 30-year-improvement, the time needed for transformation is still 1.5–3.0 hours because the host cells are injured by the chemical treatment. The injured host cells require a recovering step. In the recovering step, the host cells are cultured in a nutrient medium to allow the injured host cells to recover their physiological function and drug resistance. Then the host cells are plated on a selective medium to screen the successfully transformed host cells. Otherwise, the transformation efficiency would decrease by several times. Recently, a fast transformation method called electroporation has been developed. Although the electroporations can deliver DNA molecules into the *E. coli* host cells by transient current, the host cells after the transient current treatment still need an hour of recovery to obtain a higher transformation efficiency (Dower et. al., 1988 *Nucleic Acids Res.* 16: 6127–6145). In 1988, Golub E. I. (*Nucleic Acids Res.* 16: 1641) also published a method of one-minute transformation. Although a recovering step is performed, the transformation efficiency is only $10^4$–$10^5$ colonies/μg plasmid DNA.

SUMMARY

It is therefore an objective of the present invention to provide a fast method of transforming competent cells to save operation time.

In a preferred embodiment of the present invention, the fast transformation method comprises the following steps. The competent cells in a container are thawed at room temperature or in a water bath. Plasmid DNAs and competent cells are mixed together in the container, and then the mixture is subjected to heat shock treatment for about 0–180 seconds. After plating the mixture on a selective medium of about 0° C.–30° C. by a plating tool of about −90° C.–30° C., the mixture is cultured on the selective medium to obtain competent cells.

In another preferred embodiment, a step of incubating the competent cells in an ice bath can be inserted between the mixing step and the heating step for about 0–90 minutes. Another step of incubating the competent cells in an ice bath can be inserted between the heating step and the plating step for about 0–60 minutes.

As described above, the recovering step of the conventional transformation method is omitted, and the transformed cells are directly plated on a low-temperature selective medium by a low-temperature plating tool. Therefore, in contrast with the conventional required recovery time of 1.5–3.0 hours, the method according to the present invention needs only several minutes, and possibly as little as several seconds.

In addition to the short operation time, another advantage of the fast transformation method is that one container can be used from the thawing step to the plating step. Therefore, an automatic transformation apparatus can be used to conduct the fast transformation method of competent cells as described above.

In the fast transformation method conducted by an automatic transformation apparatus, competent cells are first thawed in a container held in a first tank at room temperature. Then, plasmid DNAs are pipetted into the container to mix with the competent cells in the container to form a mixture by a micropipette. Next, the container is transferred by a robot arm to a second tank heated by a temperature control unit for about 0–180 seconds, whereby the mixture in the container is subjected to heat shock treatment. A plate filled with a selective medium at about 0–30° C. and a plating tool of about −90° C. to 30° C. on the selective medium are provided by a plate-loading unit. The plating tool is moved on the selective medium to spread the mixture thereon by the plating unit. Finally, the mixture is cultured on the selective medium in an incubating unit to obtain transformed cells.

It is to be understood that both the foregoing general description and the following detailed description are by examples, and are intended to provide further explanation of the invention as claimed.

DESCRIPTION OF THE PREFERRED EMBODIMENTS

The recovering step of a conventional transformation method is the most time-consuming and troublesome step. In the recovering step, new tubes with SOC or LB culture solutions are needed, and then the tubes with culture solution and transformed cells need to be incubated at 37° C. with shaking for at least 1–2 hours. If the recovering step can be omitted or the time needed for the recovering step can be reduced, the transformation method can be largely simplified.

In a conventional transformation method, a recovering step of culturing the transformed cells, which have absorbed plasmid DNAs capable of resisting antibiotics, in a SOC or LB culture solution at 37° C. with shaking for 1.0–2.0 hours is usually performed before a plating and a selective step. The purpose of the recovering step is to allow the transformed cells time to express the antibiotic resistance of the absorbed plasmid DNAs. Hence the transformed cell can survive in a selective medium with antibiotics in the selective step. If the time needed for the recovering step is reduced, the injury to the host cells during the steps of thawing, incubating in a ice bath, and heat shock also have to be reduced to make the transformed cells develop antibiotic resistance more rapidly.

In a preferred embodiment of the present invention, the fast transformation method comprises the following steps. The competent cells in a tube are thawed at room temperature or in a water bath. Plasmid DNAs and competent cells are mixed together in the tube, and then the mixture is subjected to heat shock treatment. After plating the mixture on a low-temperature selective medium by a low-temperature plating tool, the competent cells are cultured on the selective medium.

In this preferred embodiment of the present invention, the transformed cells are directly plated on the selective medium at a low temperature, and the conventional recovering step, which is usually performed before the plating and selective step, is omitted. Therefore, the drawbacks of the conventional transformation method, such as multiple steps (multiple tubes) and time-consumption (about 1.5–3.0 hours) are overcome by the advantages of the present invention, such as a short time (several seconds to several minutes) and use of a single tube.

Generally, competent cells are stored at −70° C. Before mixing plasmid DNAs and competent cells, the competent cells first have to be thawed. A method of thawing the competent cells is incubating them for about 5–3 minutes in an ice bath for slow thawing. A method of fast thawing the competent cell is to incubate them in a water bath for about 5 seconds to 5 minutes.

The competent cells can be prepared form, for example, various Escherichia coli (E. coli) strains such as HB101, DH5α, GM2929, XL1-Blue, TG1, BL21, and JM109 etc. E. coli is the most widely applied microorganism. Especially in the field of molecular biology and genetic engineering, E. coli variants are obligate host cells used in labs for mass-producing different kinds of DNAs or proteins.

Then, plasmid DNAs and the competent cells are mixed together. No special limiting conditions are needed for the competent cells. The competent cells can be purchased from any commercial available sources or made according to any known technology. The plasmid DNAs can be obtained from any natural sources or after recombination by genetic engineering. The competent cells and the plasmid DNAs can be mixed either by gently inverting the tube with the fingers or by violently shaking the tube with a shaker.

After uniformly mixing, the mixture of the plasmid DNAs and the competent cells are incubated in an about 36–48° C. water bath for heat shock treatment. The time needed for the heat shock treatment is preferably for about 0–180 seconds and more preferably for about 10–90 seconds.

Next, the mixture is plated on a low-temperature selective medium by a low-temperature plating tool. The plating tool can be a conventional one such as glass beads or a glass loop. The temperature of the plating tool is preferably about −90° C.–30° C. and more preferably about −20° C.–8° C. The temperature of the selective medium is preferably about 0° C.–30° C. and more preferably about 0° C.–4° C.

Finally, the competent cells are cultured on the selective medium. An antibiotic is added to the selective medium. The amount of the antibiotic added can be varied as needed or according to the known arts. For example, the concentration of an antibiotic such as ampicillin can be about 25–100 µg/mL.

According to another preferred embodiment of the present invention, a step of incubating in an ice bath can be inserted between the mixing step and the heat shock step. That is, after mixing the plasmid DNAs and the competent cells, the mixture is incubated in an ice bath then subjected to the heat shock treatment. The time for the mixture incubated in the ice bath is preferably about 0–90 minutes and more preferably about 0–30 minutes. Another step of incubating in an ice bath can be inserted between the heat shock treatment and the plating step. The time for incubating the mixture in the ice bath is preferably about 0–60 minutes and more preferably about 0–30 minutes.

Without further elaboration, it is believed that the above description has adequately enabled the present invention. The following specific examples are, therefore, to be construed as merely illustrative, and not limitative of the remainder of the disclosure in any way whatsoever. All of the publications cited herein are hereby incorporated by references on their entire.

Preparation of Competent Cells

The competent cells of the present invention were produced by the following four chemical methods. The four chemical methods are $CaCl_2$ (Mandel, M., and Higa A. 1970, J. Mol. Biol. 53: 159–162), TB (Inoue H, 1990, Gene 96: 23–28), TSS (Chung C. T., Proc. Natl. Acad. Sci. USA., 86:2172–2175), and TFB (Hanahan D., 1983, J. Mol. Bio. 166: 557–580). The strain of E. coli used was DH5α, which is commonly used in the research of molecular biology. The genetic information of DH5α strain is F⁻ (Φ80d lacZΔM15) Δ (lacZYA-argF) U169 supE44 hsdR17($r_K$–$m_K$+) recA1 gyrA96 endA1 thi-1 relA1 deoR λ⁻.

In the transformation procedures, a clone of the DH5α strain was inoculated in a LB culture solution and cultured at about 37° C. for about 16 hours. The cells of the DH5α strain were then diluted by the LB culture solution to a concentration of about 1/100 of the original concentration. The diluted DH5α strain cells solution was divided into four bottles and was continuously cultured in the LB culture solution until the absorbance was about 0.2–0.6. Then, the competent cells were respectively produced by the four chemical methods described above (Methods in Enzymology, 1991, 204:63–113) and stored at about −70° C.

The Efficiency of the Conventional Transformation Method

EXAMPLE 1

The competent cells prepared by the four chemical methods as described in the section, PREPARATION OF COMPETENT CELLS, were transformed by plasmid pUC19. The operation steps and times are shown in Table 1. The tested concentration of the plasmid pUC19 is $10^{-4}$ or $10^{-5}$ µg/µL, and the amount used was 1 µL for each time. The amount of the competent cells used was 100 µL every time. Thawing was conducted according to the various transformation methods described in Methods in Enzymology, 1991, 204:63–113. As shown in Table 1, the time needed for the conventional transformation method was about 1.5–3.0 hours.

TABLE 1

Operation steps and time needed of the conventional transformation methods (CaCl2, TSS, TB and TFB).

| Operation Step | Operation Time |
|---|---|
| Thawing competent cells | 5–30 minutes |
| Adding and mixing plasmids with the competent cells | About 1 minute |
| Incubating the mixture in an ice bath | 10–30 minutes |
| Heat shock treatment | 0–2 minutes |
| Incubating the mixture in an ice bath | 2–15 minutes |
| Adding SOC or LB culture solution | 1–5 minutes |
| Culturing the competent cells at 37° C. with shaking | 60–120 minutes |
| Plating the competent cells on a selective medium (LB + antibiotic*) at room temperature or at 37° C. | 3–10 seconds |

*The added concentration of the antibiotic is usually, for example, 25–60 µg/mL for ampicillin. The 40 µg/mL ampicillin in the LB agar gel, which is abbreviated as LBAp40, was used by the present invention for series of tests.

The transformation efficiencies of the competent cells prepared by the four chemical methods described above are listed in Table 2. The results match the results published in the relevant literature. Hence, the competent cells prepared in the section, PREPARATION OF COMPETENT CELLS, can be used to test the transformation method of the present invention.

TABLE 2

The transformation efficiencies of the competent cells
prepared by the four chemical methods described in the section,
PREPARATION OF COMPETENT CELLS.

| Preparation methods of<br>The competent cells | Transformation efficiency<br>(transformed clone/μg pUC19) |
|---|---|
| $CaCl_2$ | $5.8 \times 10^7$ |
| TB | $1.2 \times 10^7$ |
| TSS | $5.0 \times 10^6$ |
| TFB | $2.7 \times 10^7$ |

The Time Effect of Each Step

EXAMPLES 2–14

Since many commercialized chemical competent cells are prepared by modified TFB (summarized from the instruction manuals of competent cells purchased from Stratagene, Promega, Invitrogen and Life Technologies), the competent cells prepared by TFB (abbreviated as TFB competent cells) were used in the following tests. Results of Examples 2–14 showed the time effect of every step to the transformation efficiency (Table 3).

competent cells. Then, the plasmid DNAs and the competent cells were uniformly mixed by fingers flipping the tube. The rest steps are listed in Table 3.

Surprisingly, the total operation time of the transformation process, except the plating step, can be reduced to 45 seconds, as shown by Example 2 in Table 3. The steps of placing the mixture of the plasmid DNAs and the competent cells on ice, which is before and after the heat shock step, and the culturing step in the transformation process can omitted. The transformation efficiency of the Example 2 is comparable to those of the conventional transformation methods in Table 2.

The Temperature Effect of the Plating Tool and the Selective Medium

The four kinds of competent cells prepared by the chemical methods described in the section, PREPARATION OF COMPETENT CELLS, were transformed by the procedure of Example 2. However, the plating tool, 4 mm glass beads, of different temperatures and the selective medium, LBAp40, at room temperature or at 4° C. were used for testing the temperature effect of the plating tool and the

TABLE 3

The effect of operation time for each step to the transformation efficiency.

| Example | Incubating the mixture in ice bath (min) | Heat shock in 42° C. water bath (sec) | Incubating the mixture in ice bath (min) | Cultured in 37° C. SOC culture solution with shaking (min) | Plating on LBAp40 medium by 4 mm glass beads at room temperature (sec) | Transformation efficiency (number of transformed clone/μg pUC19) |
|---|---|---|---|---|---|---|
| 2 | 0 | 45 | 0 | 0 | 3–10 | $1.6 \times 10^7$ |
| 3 | 0 | 45 | 0 | 30 | 3–10 | $5.1 \times 10^7$ |
| 4 | 0 | 45 | 0 | 60 | 3–10 | $6.2 \times 10^7$ |
| 5 | 0 | 45 | 5 | 30 | 3–10 | $5.9 \times 10^7$ |
| 6 | 0 | 45 | 5 | 60 | 3–10 | $4.2 \times 10^7$ |
| 7 | 30 | 45 | 15 | 30 | 3–10 | $4.9 \times 10^7$ |
| 8 | 30 | 45 | 15 | 60 | 3–10 | $7.2 \times 10^7$ |
| 9 | 30 | 45 | 15 | 30 | 3–10 | $5.0 \times 10^7$ |
| 10 | 30 | 45 | 15 | 60 | 3–10 | $6.3 \times 10^7$ |
| 11 | 30 | 0 | 0 | 30 | 3–10 | $4.0 \times 10^7$ |
| 12 | 30 | 0 | 0 | 60 | 3–10 | $5.0 \times 10^7$ |
| 13 | 60 | 0 | 0 | 30 | 3–10 | $2.5 \times 10^6$ |
| 14 | 60 | 0 | 0 | 60 | 3–10 | $3.5 \times 10^6$ |

The transformation process started from fast thawing the competent cells stored in refrigerator in 25° C. water bath for about 5–20 seconds. When ½–¼ of the competent cells are in thawed state, the plasmid DNAs was added to the selective medium. The results are shown in Table 4. From the results in Table 4, it shows that the plating tool and the selective medium at low temperature can increase the transformation efficiency of the competent cells.

TABLE 4

The temperature effect of the plating tool and the selective medium to the transformation efficiency.

| Temp. of 4 mm glass beads | Transformation Efficiency (transformed clones/μg pUC19) | | | | | | |
|---|---|---|---|---|---|---|---|
| | LBAp40 at room temperature | | | LBAp40 at 4° C. | | | |
| | $CaCl_2$* | TB* | TFB* | $CaCl_2$* | TB* | TSS* | TFB* |
| 30° C. | $4.0 \times 10^4$ | $1.0 \times 10^6$ | $1.4 \times 10^7$ | $8.0 \times 10^4$ | $1.6 \times 10^6$ | — | $3.5 \times 10^7$ |
| 8° C. | $2.2 \times 10^5$ | $1.3 \times 10^6$ | — | $6.4 \times 10^5$ | $4.2 \times 10^6$ | — | — |
| 4° C. | $6.0 \times 10^4$ | $4.2 \times 10^5$ | — | $1.4 \times 10^7$ | $2.2 \times 10^6$ | $1.2 \times 10^6$ | $1.1 \times 10^8$ |
| 0° C. | $5.4 \times 10^5$ | $1.4 \times 10^6$ | — | $8.4 \times 10^6$ | $4.8 \times 10^6$ | — | — |
| −20° C. | $3.4 \times 10^5$ | $3.7 \times 10^6$ | — | $9.6 \times 10^6$ | $1.6 \times 10^7$ | — | $1.6 \times 10^8$ |
| −80° C. | — | — | — | — | — | — | $4.6 \times 10^7$ |

*The competent cells are respectively prepared by chemical methods of $CaCl_2$, TB, TSS, and TFB.

The Time Effect of the Heat Shock Treatment

EXAMPLES 15–22

The four kinds of competent cells prepared by the chemical methods described in the section, PREPARATION OF COMPETENT CELLS, were transformed by the procedure of Example 2. The glass beads and the LBAp40 medium both were at 4° C. However, the treating time of the heat shock (42° C. water bath) was varied to test the time effect of the heat shock treatment. The results are shown in Table 5.

TABLE 5

The time effect of the heat shock treatment to the transformation efficiency.

| Examples | Heat shock treatment (sec) | Transformation Efficiency (transformed clones/µg pUC19) |
|---|---|---|
| 15 | 0 | $4.0 \times 10^7$ |
| 16 | 10 | $1.4 \times 10^8$ |
| 17 | 25 | $1.7 \times 10^8$ |
| 18 | 45 | $1.3 \times 10^8$ |
| 19 | 60 | $1.2 \times 10^8$ |
| 20 | 90 | $1.4 \times 10^8$ |
| 21 | 120 | $9.6 \times 10^7$ |
| 22 | 180 | $4.0 \times 10^7$ |

From Table 5, the transformation efficiency without heat shock treatment (Example 15) is comparable to those with heat shock treatment (Examples 16–22). The transformation efficiency of the heat shock treatment is better for about 10–90 seconds (Examples 16–20). Therefore, from the results of Tables 3 and 5, even the time of the cold and heat treatment was reduced and the step of recovering in LB or SOC culture solution was omitted, a comparable or even a better result than that of the conventional method can be obtained. The transformation efficiencies are closed to those under the commercialized standard.

The Applicability of the Fast Transformation Method

The competent cells were prepared by the TB and TFB method described in the section, PREPARATION OF COMPETENT CELLS. The strains used of *E. Coli* were DH5α and JM109, and the plasmid DNAs used were pUC19, pBR322, and pUC4K as shown in Table 6.

TABLE 6

Data of plasmids pUC19, pBR322, and pUC4K.

| Plasmid | Molecular Weight (Kb) | Selection Marker (Drug Resistance Gene) | Replicative Origin |
|---|---|---|---|
| pUC19 | 2.7 | $Ap^r$ | Mutant pMB1 |
| pUC4K | 4.0 | $Ap^r\ Km^r$ | Mutant pMB1 |
| pBR322 | 4.3 | $Ap^r\ Tc^r$ | Mutant pMB1 |

The antibiotics added to the selective medium were Ampicillin (Ap), Kanamycin (Km), Tetracyclin (Tc), Ap/Km, and Ap/Tc. The plating tool, the glass beads, and the selective medium used were at 4° C. The results are shown in Table 7. From Table 7, it is shown that the transformation efficiencies were higher than $10^6$ transformed clones/µg plasmid. Hence the fast transformation method has a wide applicability to various *E. Coli* strains, plasmids, and selective medium.

TABLE 7

Applicability of the fast transformation method to different strains, plasmids, and antibiotics.

| Strain | Method of preparing competent cells | Plasmid[1] | Transformation Efficiency (transformed clones/µg plasmid) | | | | |
|---|---|---|---|---|---|---|---|
| | | | $Ap^2$ | $Km^2$ | $Tc^2$ | $Ap/Km^2$ | $Ap/Tc^2$ |
| DH5α | TFB | pUC19 | $1.7 \times 10^8$ | — | — | — | — |
| | | pBR322 | $3.8 \times 10^7$ | — | — | — | $1.2 \times 10^7$ |
| | | pUC4K | $1.7 \times 10^8$ | $3.2 \times 10^7$ | — | $1.1 \times 10^7$ | — |
| | TB | pUC19 | $4.0 \times 10^7$ | — | — | — | — |
| | | pBR322 | $5.0 \times 10^6$ | — | — | — | $3.0 \times 10^6$ |
| | | pUC4K | $4.0 \times 10^7$ | — | — | $5.0 \times 10^6$ | — |
| JM109 | TFB | pUC19 | $5.2 \times 10^7$ | — | — | — | — |
| | | pBR322 | $7.0 \times 10^7$ | — | $4.0 \times 10^7$ | — | — |
| | | pUC4K | $4.0 \times 10^7$ | $1.6 \times 10^7$ | — | — | — |
| | TB | pUC19 | $1.0 \times 10^7$ | — | — | — | — |
| | | pBR322 | $3.2 \times 10^6$ | — | $2.0 \times 10^6$ | — | — |
| | | pUC4K | $7.2 \times 10^6$ | $1.0 \times 10^6$ | — | — | — |

[1]The amount of the plasmids used was $10^{-4}$ µg/transformation.
[2]The concentrations of the antibiotics used for Ap, Km, and Tc respectively were 40 µg/mL, 25 µg/mL, and 12.5 µg/mL.

The Shape Effect of the Plating Tool

The transformation efficiency was not much affected by using glass beads or glass loop as the plating tool (the results are not shown). Therefore, the shape of the plating tool did not have pronounced effect to the transformation efficiency.

The Practical Application to the Yea Competent Cells

EXAMPLES 23–39

The YEA competent cells (a DH5α-derived strain which was prepared by TFB method) of the Yeastern Biotech Co., Ltd. were transformed by the conventional transformation method (2 hours' protocol). The transformation efficiency was $1 \times 10^8 – 5 \times 10^8$ transformed colonies/µg plasmid for the YEA competent cells.

The YEA competent cells were also transformed by the fast transformation method provided of the present invention. The YEA competent cells stored in the refrigerator was fast thawed in 25° C. water bath for about 5–20 seconds. When ½–¼ of the competent cells are in thawed state, the plasmid DNAs was added to the competent cells. Then, the plasmid pUC19 and the competent cells were uniformly mixed by flipping the tube. The plating tool, glass beads, and the selective medium were stored at 4° C. The rest steps are listed in Table 8.

From the experimental results shown in Table 8, it is proved that the time needed is reduced from the 1.5–3.0 hours (Table 1) of the conventional transformation method to less than 1 minute (Examples 23 and 29–31 in Table 8) of the fast transformation method. The transformation efficiency listed in Table 8 of the fast transformation method can reach $10^{7–109}$ pUC19.

TABLE 8

The transformation efficiency of the YEA competent cells

| Example | Incubating the mixture in ice bath (min) | Heat shock in 42° C. water bath (sec) | Incubating the mixture in ice bath (min) | Cultured in 37° C. SOC culture solution with shaking (min) | Transformation efficiency (transformed clone/µg pUC19) |
|---|---|---|---|---|---|
| 23 | 0 | 0 | 0 | 0 | $8.0 \times 10^7$ |
| 24 | 5 | 0 | 0 | 0 | $4.0 \times 10^7$ |
| 25 | 15 | 0 | 0 | 0 | $5.2 \times 10^7$ |
| 26 | 30 | 0 | 0 | 0 | $1.7 \times 10^8$ |
| 27 | 60 | 0 | 0 | 0 | $9.5 \times 10^7$ |
| 28 | 90 | 0 | 0 | 0 | $9.0 \times 10^7$ |
| 29 | 0 | 10 | 0 | 0 | $1.4 \times 10^9$ |
| 30 | 0 | 25 | 0 | 0 | $1.7 \times 10^9$ |
| 31 | 0 | 45 | 0 | 0 | $1.6 \times 10^9$ |
| 32 | 0 | 45 | 30 | 0 | $2.4 \times 10^8$ |
| 33 | 0 | 45 | 60 | 0 | $3.2 \times 10^8$ |
| 34 | 30 | 45 | 0 | 0 | $5.8 \times 10^8$ |
| 35 | 30 | 45 | 30 | 0 | $6.0 \times 10^8$ |
| 36 | 30 | 45 | 30 | 60 | $2.3 \times 10^8$ |
| 37 | 30 | 45 | 60 | 0 | $6.4 \times 10^8$ |
| 38 | 60 | 45 | 0 | 0 | $4.2 \times 10^8$ |
| 39 | 60 | 45 | 30 | 0 | $3.2 \times 10^8$ |

TABLE 9

The applicability of the fast transformation to the various strains of *E. coli*.

| Transformation Efficiency | Strains | Genome Type | Remarks |
|---|---|---|---|
| $10^7–10^8$ | HB101 | F-leuB6 proA2 recA13 thi-1 ara-14 lacY1 galK2 xyl-5 mtl-1 rpsL20 supE44 hsdS20 | |
| $10^8–10^{10}$ | DH5α | F⁻ (Φ80d lacZΔM15) Δ(lacZYA-argF)U169 supE44 hsdR17($r_K^-$ $m_K^+$) recA1 gyrA96 endA1 thi-1 relA1 deoR λ⁻ | A host for pUC and other α-complementation vectors. It is useful for DNA cloning. |
| $10^7–10^8$ | GM2929 | F- dam-13::Tn9 dcm-6 hsdR2 recF143 galK2 galT22 ara-14 lacY1 xyl-5 thi-1 tonA31 rpsL136 hisG4 tsx-78 mtl-1 glnV44 leuB6 rfbD McrA- McrB- | It has become the standard dam dcm double mutant strain. It is deficient for plasmid recombination and lacks the Mcr and Hsd restriction systems. The strain transforms well with plasmid DNA. It is derived from GM2163. |
| $10^8–10^{10}$ | XL1-Blue | recA1 endA1 gyrA96 thi-1 hsdR17 supE44 relA1 lac [F' proAB lacI^qZΔM15 Tn10 (Tet^r)] | |
| $10^7–10^8$ | TG1 | F', thi, Δ(lac-proAB), hsdR4(Δ5), supE44 (F':traD36, proAB+, lacIq, lacZΔM15) | It does not modify or restrict transfected DNA and supports growth of vectors carrying amber mutations. |
| $10^7–10^8$ | BL21 | *E. coli* B F⁻ dcm omp T hsdS($r_B^-$ $m_B^-$) gal | |
| $10^8–10^{10}$ | JM109 | F' traD36 proA+ proB+ lacIq Δ(lacZ)M15 Δ(lac-proAB) supE44 hsdR17 recA1 gyrA96 thi-1 endA1 relA1 e14- λ- | It is defective in cell wall synthesis. It is mucoid colonies and a transformation host. This is a host for M13 and other filamentous bacteriophages. |

Competent cells of other E. coli strains were also prepared by the same method as that by which the YEA competent cells were prepared and also were transformed by the fast transformation method. The transformation efficiencies (listed in Table 9), $10^7$–$10^{10}$ transformed colonies/μg plasmid, also reach the commercialized standard, which is also $10^7$–$10^{10}$ transformed colonies/μg plasmid. The transformation efficiency listed in Table 9 may be slightly insufficient when compared to the higher level of cloning such as genomic libraries or cDNA libraries but is sufficient for the general cloning, such as subcloning or TA cloning, for molecular biology experiments.

Automatic Fast Transformation

In addition to the short operation time, another advantage of the fast E. Coli transformation method is that one tube can be used from the thawing step to the plating step. Therefore, a large number of transformations can be performed at the same time by the fast transformation method. For example, 24, 96, 384 or even more transformations can be performed in an arrayed arrangement.

Further, an automatic transformation apparatus can be used to conduct the fast E. coli transformation method to save time and cost due to the need for only one tube in the fast transformation method and omission of the recovering step. The automatic transformation apparatus comprises, for example, a temperature control unit, a micropipette, a robot arm, a plate loading unit, a plating unit and an incubating unit.

A temperature control unit is used to control the different temperatures of different tanks such as dry bath blocks for holding containers containing the plasmids and/or competent cells, or the selective medium in the steps of thawing, heat shock and cold shock. The container can be, for example, a multi-well plate. The robot arm is used to transfer the container between tanks with different temperatures.

A micropipette such as a multi-channel micropipette is used to pipette the plasmid DNAs into the container and mix them. The micropipette is also used to pipette the mixture on the selective medium. A plate-loading unit is used to stack and provide plates filled with a selective medium at about 0–30° C. The plating unit is used for providing and moving, such as horizontally or orbitally shaking, the plating tool on the selective medium to uniformly spread the mixture on the selective medium. The plating tool can be, for example, 4 mm glass beads. Then, the robot arm can remove the plating tool on the selective medium after the plating step is performed. The incubating unit is used to provide a suitable temperature such as about 37° C. for growing the competent cells on the selective mediums in the plates.

A preferred embodiment is provided here. Each plate with about 8–10 glass beads and a collection plate having multiple wells, such as about 8–384 wells, is prepared. The collection plate can be, for example, an ELISA plate. Competent cells stored at about −70° C. are added to the wells with an amount of about 10–200 μL/well.

The collection plate is placed on a manifold base, and about 0.1–20 μL of plasmid DNAs are added to each well. Then, the competent cells and the plasmid DNAs are completely mixed to form a mixture by shaking in a shaker for 2–5 seconds or pipetting the mixture in the wells up and down 2–3 times with a multi-channel micropipette. The collection plate is transferred to a heater or a dry bath block by a robot arm, and then the collection plate is heated at about 42° C. for about 0–180 seconds to perform the heat shock treatment.

Plates filled with a selective medium are moved from a plate-loading unit to the manifold base by the robot arm. The transformed cells are pipetted from the wells to the selective medium by the multi-channel micropipette, and glass beads are added to the selective medium by a plating unit. The plating unit moves the glass beads on the selective medium to uniformly spread the transformed cells thereon. Then, the robot arm tips the plates to pour out the glass beads. Next, the plates are placed in an incubating unit at about 37° C. for 12–20 hrs to culture the competent cells to obtain transformed cells.

Due to the combination of the transformation performed in an arrayed arrangement with the automatic apparatus, a large number of transformations can be automatically performed to obtain a large number of various transformed cells at the same time.

Broad Range of Applications in Bacteria Transformed Via Chemical Method

Since most of the competent cells are prepared by the modified TFB method as stated in the operation manual of Stratagene, Invitrogen, Promega, and Life Technologies companies, the fast transformation method can applied to most commercial competent cells. Furthermore, the operation time can be reduced from about 1.5–3.0 hours to several minutes or as little as several seconds without reducing the transformation efficiency when the fast transformation method is applied.

Besides, E. coli is Gram negative and the preparation of the most competent cells of Gram negative or Gram positive bacteria is modified from the transformation method of E. coli (Method In Enzymology 204: 63–113, Method in Microbiology 21: 79–128). Therefore, the fast transformation method may applied to the transformation of competent cells of Gram negative or Gram positive bacteria transformed via chemical treatment. Examples can be found in "Methods in Microbiology 21: 79–128". The examples listed include *Aerobacter aerogenes, Agrobacterium tumefaciens, Alcaligenes eutrophus, Azotobacter vinelandii, Bacillus brevis, Bacillus subtillus, Erwinia carotovora, Erwinia amylovora, Erwinia herbicola, Pseudomonas aureginosa, Pseudomonas phaseolicola, Pseudomonas syringae, Proteus vulgaris, Rhizobium meliloti, Salmonella typhimurium, Serratia marcescens, Staphylococcus aureus, Streptococcus faecalis, Streptococcus lactis, Streptomyces lividans,* and *Xanthomonas campestris.*

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A fast method of transforming competent cells, comprising:

thawing competent cells, prepared from *Escherichia Coli,* in a container at room temperature or in a water bath;

mixing a plasmid DNA and the competent cells in the container to form a mixture;

plating the mixture on a selective medium of about 0° C. to less than room temperature by a plating tool of about −90 ° C. to less than room temperature without heating the mixture and recovering the competent cells in a culture medium before the plating step; and culturing the mixture on the selective medium to obtain transformed cells.

2. The fast transformation method of claim 1, wherein the thawing step is performed for about 5 seconds to about 5 minutes.

3. The fast transformation method of claim 1, wherein the plasmid DNA comprises recombinant DNA.

4. The fast transformation method of claim 1, wherein the plating tool comprises glass beads or a glass loop.

5. The fast transformation method of claim 1, wherein the selection medium comprises a medium with an antibiotic added thereto.

6. The fast transformation method of claim 1, wherein the method is performed in an arrayed arrangement by an automatic transformation apparatus.

7. The fast transformation method of claim 1, wherein the thawing step is performed until about ½ to ¼ of the competent cells are in a thawed state.

8. The fast transformation method of claim 1, wherein the temperature of the plating tool is about −20° C. to 8° C.

9. The fast transformation method of claim 1, wherein the temperature of the selection medium is about 0–4° C.

10. A fast method of transforming competent cells, comprising:

thawing competent cells, prepared from *Escherichia Coli*, in a container at room temperature or in a water bath;

mixing a plasmid DNA and the competent cells in the container to form a mixture;

heating the mixture in the container for about 0–180 seconds to perform heat shock plating the mixture on a selective medium of about 0° C. to less than room temperature by a plating tool of about −90° C. to less than room temperature without recovering the competent cells in a culture medium before the plating step; and culturing the mixture on the selective medium to obtain transformed cells.

11. The fast transformation method of claim 10, wherein between the steps of mixing and heating further comprises a step of incubating the mixture in an ice bath for about 0–90 minutes.

12. The fast transformation method of claim 10, wherein between the steps of mixing and heating further comprises a step of incubating the mixture in an ice bath for about 0–30 minutes.

13. The fast transformation method of claim 10, wherein between the steps of heating and plating further comprises a step of incubating the mixture in an ice bath for about 0–60 minutes.

14. The fast transformation method of claim 10, wherein between the steps of heating and plating further comprises a step of incubating the mixture in an ice bath for about 0–30 minutes.

15. The fast transformation method of claim 10, wherein the heat shock is performed at a temperature of about 36–48° C.

16. The fast transformation method of claim 10, wherein the heat shock is performed for about 10–90 seconds.

* * * * *